United States Patent [19]

Lapis et al.

[11] 4,260,595
[45] Apr. 7, 1981

[54] PHARMACEUTICAL COMPOSITIONS AND PROCESS FOR THE PREPARATION OF SAME

[75] Inventors: Karoly Lapis; Bela Szende; Andreas Jeney; Laszlo Kopper; Karoly Simon; Erno Tyihak; Lajos Kisfaludy; Lajos Kovacs; György Dobo, all of Budapest, Hungary

[73] Assignee: Richter Gedeon Vegyeszeti Gyar Rt., Budapest, Hungary

[21] Appl. No.: 950,579

[22] Filed: Oct. 12, 1978

[30] Foreign Application Priority Data

Oct. 13, 1977 [HU] Hungary .................................. RI 649

[51] Int. Cl.³ .................. A61K 31/195; A61K 31/66; A61K 31/475

[52] U.S. Cl. ..................................... 424/10; 424/319; 424/209; 424/262

[58] Field of Search ................... 424/319, 10, 209, 262

[56] References Cited

PUBLICATIONS

Chemical Abstracts, 85: 117749x (1976).

Primary Examiner—Jerome D. Goldberg
Attorney, Agent, or Firm—Karl F. Ross

[57] ABSTRACT

There are disclosed pharmaceutical compositions comprising at least one cytostatic agent and $N^\epsilon$-trimethylthyllysin or a pharmaceutically acceptable salt thereof, optionally in association with conventional pharmaceutical carriers and other additives.

The new compositions possess a reduced toxicity compared with the cytostatic agents administered alone.

4 Claims, 6 Drawing Figures

PHARMACEUTICAL COMPOSITIONS AND PROCESS FOR THE PREPARATION OF SAME

This invention relates to new pharmaceutical compositions a process for the preparation of same. More particularly, according to this invention there are provided pharmaceutical compositions comprising a combination of one or more known cytostatic agents and $N^\epsilon$-trimethyllysin (hereinafter abbreviated as TML) for an active ingredient for treatment of animal subjects.

The new pharmaceutical compositions of the invention possess cytostatic activity for animal subjects the extent of which corresponds to the quantity of the cytostatic agent present in the composition, or is even higher; however hand the compositions are devoid of the undesired side-effects which are characteristic of the known cytostatics, and make themselves felt in damage to the bone marrow, and accelerating the restitution following accidental damage.

It is well known that the chemotherapy of malignant tumors is considerably hindered by the fact that all the cytostatic agents which proved to be potent in the inhibition of the proliferation of tumor cells, show a toxic side-effect against the cells of the bone marrow and other intensively proliferating tissues (such as intestinal mucosa, gonads). Since the haemopoeticus and the immune system are seriously damaged, this side-effect finally results in the death of the patient.

The present invention aims at reducing the toxicity of the various cytostatic agents and accelerating the rate of restitution following the damage in animal subjects.

It has now been found that the toxicity of the cytostatic agents is considerably decreased when they are administered the organism in combination with TML. This discovery is highly surprising in view of the fact that to the present time TML has known to exert a tumor growth promoting activity [Szende et al., Neoplasma, 17, 4, 433 to 434 (1970)].

The invention is based on the perception that when a cytostatic agent is administered to an animal subject in combination with TML, which is known to accelerate the tumor growth and the proliferation of other tissues, e.g. bone marrow, the toxicity of the cytostatic agent is decreased while the latter retains a substantially unchanged or even has increased cytostatic activity.

In the pharmaceutical compositions according to the invention a large variety of natural, semi-synthetic or synthetic cytostatic compounds can be employed. Some representatives of these agents are listed below:
vinblastine,
vincristine,
leurosine, which are of natural origin;
1,4-di-(2-methylsulphophenyloxyethylamino)-1,4-didesoxyerythrite dimethylsulphonate (furtheron this compound will be designated as "ritosulfanum", a name which has been accepted by the WHO),
2[bis-(2-chloroethyl)-amino]-tetrahydro-2H-1,3,2-oxazaphosphorine-2-oxyde (cyclophosphamide) or
N-formylleurosine, which can be prepared synthetically
The above compounds are illustrative only and do not limit the scope of known cytostatics which may be used in the compositions of the invention.

In the pharmaceutical compositions according to the invention—in line with general practice—cytostatics are generally used in the form of their pharmaceutically acceptable salts. The salts—which can be acid addition or quaternary salts—are generally used because they contribute to a better and faster absorption and bring the heat- and light-sensitive free bases, which are susceptible to decomposition, such as diindole alkaloids, into a stabile form.

TML can be used either in a racemic or in an optically active form but during our experiments L-TML proved to be the most effective. TML is advantageously used in the form of a pharmaceutically acceptable acid-addition salt thereof. The acid addition salts are prepared with inorganic or organic acids, for instance with a hydrogen halide, such as hydrogen chloride, hydrogen bromide or hydrogen iodide, sulphuric acid, various acids or phosphorus, acetic acid, propionic acid, butyric acid, maleic acid, fumaric acid, citric acid, malic acid, tartaric acid, ascorbic acid, asparaginic acid, glutamic acid etc. Preferably the hydrochloride, monofumarate, acetate or an acid addition-salt formed with ascorbic acid of TML are used. The monoglutamate of TML (TML.Glu) is especially advantageously used. The salts of TML formed with one or more molecules of fumaric acid, asparaginic acid or glutamic acid are new, their preparation is described in the Hungarian patent application RI-648, dated Oct. 13, 1977 corresponding to concurrently filed U.S. application Ser. No. (attorney's docket No. 11042).

In order to prove the advantageous pharmaceutical properties of the compositions according to the invention, the harmful effect of the various cytostatic agents on the blood count was compared with a corresponding effect of the compositions, in which TML is also present. The test were carried out on 35 female CBA mice, weighing 25 g. each, in the following way:

The mice were divided into seven groups (groups a) to g)) containing five animals each. The separate groups were given the following treatment:

(a) untreated;
(b) a single 30 mg./kg. dose of ritosulfanum;
(c) a single dose of a combination of 30 mg./kg. of ritosulfanum and 20 mg./kg. of TML;
(d) a single 50 mg./kg. dose of cyclophosphamide;
(e) a single dose of a combination of 50 mg./kg. of cyclophosphamide and 20 mg./kg. of TML;
(f) a single 2 mg./kg. dose of vincristine;
(g) a single dose of a combination of 2 mg./kg. vincristine and 20 mg./kg. of TML.

The drugs were administered intraperitoneally. In some instances the TML was employed in the form of the hydrochloride salt thereof. The mg./kg. values indicate the number of mgs per kg./of body weight of the test animals.

Figure 1:
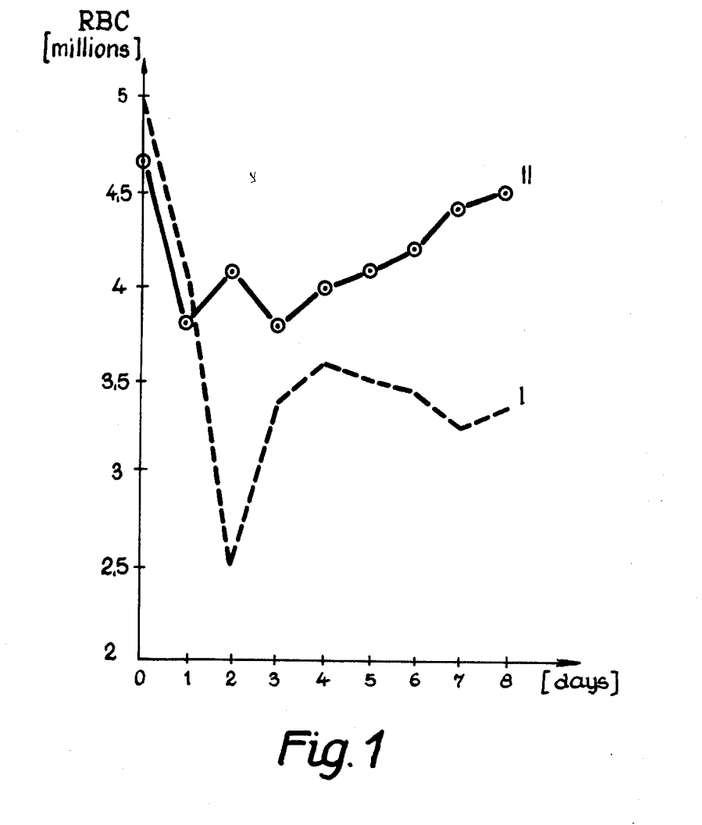
Figure 2:
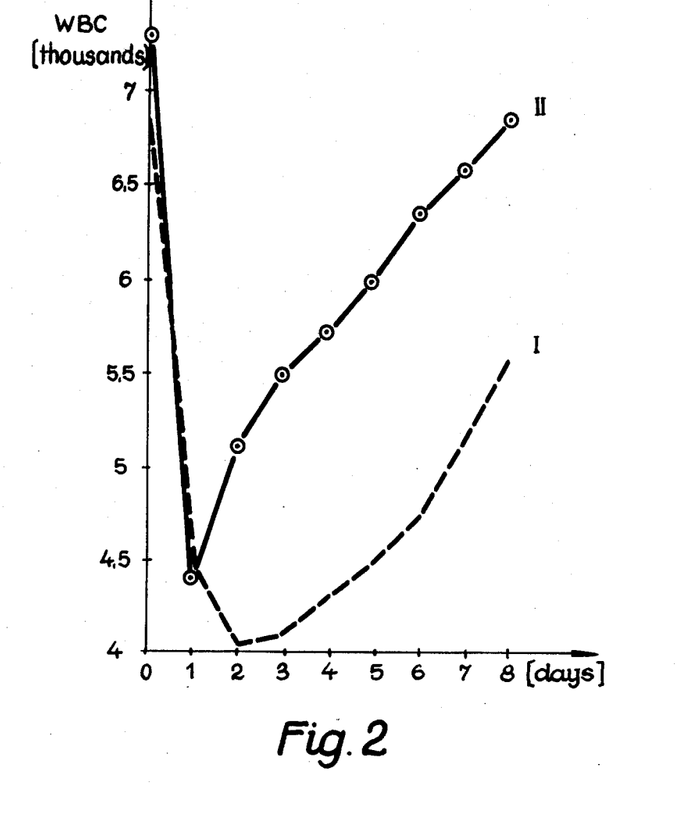

On the day preceding the treatment (indicated by 0 in the following table) and in the following 8 days, once a day, in the same time, after 16 hours of starvation the differential and quantitative peripheral blood count of the animals were determined. The results obtained are set forth in the following Tables 1 to 3 and are illustrated on FIGS. 1 to 6. Table 1 and FIGS. 1 and 2 show the results obtained with ritosulfanum; Table 2 and FIGS. 3 and 4 relate to the treatment with cyclophosphamide and in Table 3 and on FIGS. 5 and 6 the results of the treatment with vincristine are illustrated. On the Figures the dotted line indicated at I shows the change in the blood count of animals treated with the various cytostatic agents alone, while the curve II shows the results obtained with a combination of the various cytostatic agents and TML. On FIGS. 1, 3 and 5 the change of the number of red blood cells (RBC) in millions, on FIGS. 2, 4 and 6 the change in the number of white blood cells (WBC) in thousands can be seen during the eight days of the experiment.

TABLE 1

Change in the blood count induced by ritosulfanum

| Day | RBC (millions/mm$^3$) ritosulfanum | RBC (millions/mm$^3$) ritosulfanum + L-TML | WBC (thousands/mm$^3$) ritosulfanum | WBC (thousands/mm$^3$) ritosulfanum + L-TML |
|---|---|---|---|---|
| 0 | 4.95 ± 0.25 | 4.65 ± 0.15 | 6.85 ± 0.15 | 7.30 ± 0.15 |
| 1 | 4.02 ± 0.12 | 3.79 ± 0.09 | 4.50 ± 0.12 | 4.40 ± 0.10 |
| 2 | 2.51 ± 0.21 | 4.06 ± 0.07 | 4.02 ± 0.12 | 5.10 ± 0.01 |
| 3 | 3.34 ± 0.14 | 3.74 ± 0.05 | 4.07 ± 0.17 | 5.45 ± 0.15 |
| 4 | 3.55 ± 0.15 | 3.97 ± 0.07 | 4.27 ± 0.02 | 5.70 ± 0.02 |
| 5 | 3.47 + 0.17 | 4.05 + 0.05 | 4.45 + 0.15 | 5.97 + 0.17 |
| 6 | 3.41 ± 0.11 | 4.17 ± 0.10 | 4.68 ± 0.18 | 6.30 ± 0.15 |
| 7 | 3.32 ± 0.12 | 4.38 ± 0.12 | 5.10 ± 0.01 | 6.52 ± 0.15 |
| 8 | 3.30 ± 0.16 | 4.45 ± 0.15 | 5.55 ± 0.15 | 6.80 ± 0.20 |

TABLE 2

Change in the blood count induced by cyclophosphamide (CPA)

| Day | RBC (millions/mm$^3$) CPA | RBC (millions/mm$^3$) CPA+L-TML | WBC (thousands/mm$^3$) CPA | WBC (thousands/mm$^3$) CPA+L-TML |
|---|---|---|---|---|
| 0 | 4.92 ± 0.20 | 4.92 ± 0.10 | 6.35 ± 0.20 | 7.05 ± 0.20 |
| 1 | 4.19 ± 0.08 | 4.03 ± 0.05 | 3.75 ± 0.12 | 4.07 ± 0.07 |
| 2 | 3.45 ± 0.10 | 4.05 ± 0.07 | 4.15 ± 0.17 | 5.35 ± 0.15 |
| 3 | 3.60 ± 0.20 | 4.96 ± 0.10 | 4.45 ± 0.22 | 5.25 ± 0.15 |
| 4 | 3.78 ± 0.15 | 4.84 ± 0.09 | 4.75 ± 0.23 | 5.30 ± 0.17 |
| 5 | 3.82 ± 0.09 | 4.80 ± 0.12 | 4.90 ± 0.28 | 5.47 ± 0.20 |
| 6 | 3.88 ± 0.20 | 4.82 ± 0.10 | 5.15 ± 0.17 | 5.72 ± 0.22 |
| 7 | 3.90 ± 0.15 | 4.84 ± 0.08 | 5.30 ± 0.15 | 5.95 ± 0.15 |
| 8 | 3.98 ± 0.12 | 4.94 ± 0.10 | 5.75 ± 0.20 | 6.32 ± 0.12 |

TABLE 3

Change in the blood count induced by vincristine

| Day | RBC (millions/mm$^3$) vincristine | RBC (millions/mm$^3$) vincristine + L-TML | WBC (thousands/cm$^3$) vincristine | WBC (thousands/cm$^3$) vincristine + L-TML |
|---|---|---|---|---|
| 0 | 4.60 ± 0.10 | 4.60 ± 0.10 | 6.80 ± 0.20 | 6.80 ± 0.20 |
| 1 | 4.80 ± 0.15 | 4.50 ± 0.08 | 5.10 ± 0.10 | 5.30 ± 0.12 |
| 2 | 4.85 ± 0.15 | 4.80 ± 0.20 | 4.50 ± 0.15 | 4.70 ± 0.15 |
| 3 | 3.30 ± 0.08 | 4.50 ± 0.08 | 4.30 ± 0.12 | 4.70 ± 0.15 |
| 4 | 3.40 ± 0.10 | 4.60 ± 0.10 | 4.50 ± 0.15 | 4.90 ± 0.15 |
| 5 | 3.60 ± 0.12 | 4.80 ± 0.20 | 4.60 ± 0.15 | 5.10 ± 0.25 |
| 6 | 3.90 ± 0.15 | 4.80 ± 0.20 | 4.60 ± 0.17 | 5.30 ± 0.10 |
| 7 | 4.10 ± 0.10 | 4.75 ± 0.15 | 4.75 ± 0.20 | 5.50 ± 0.12 |
| 8 | 4.10 ± 0.10 | 4.60 ± 0.10 | 4.80 ± 0.20 | 5.70 ± 0.15 |

Figure 3:
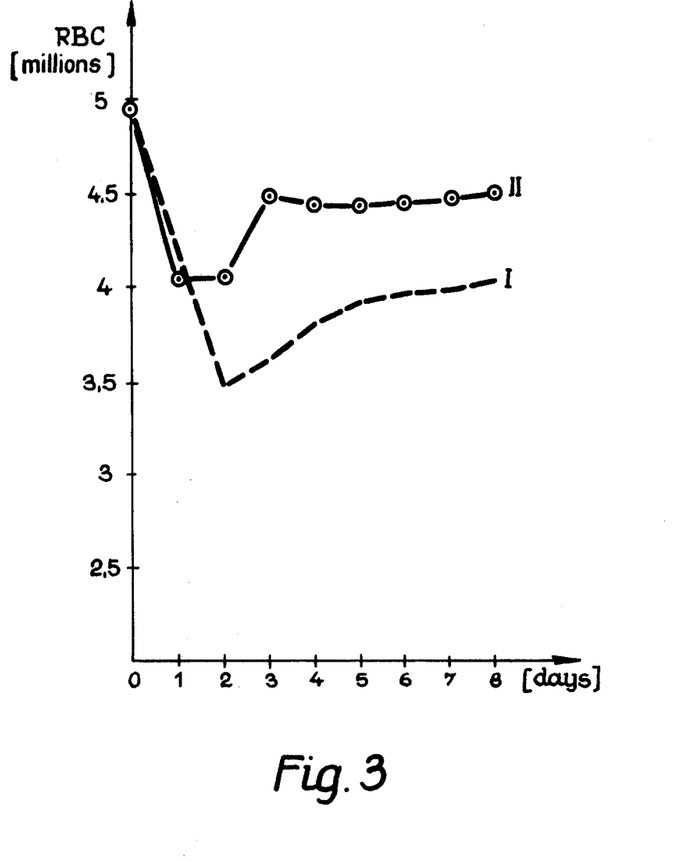
Figure 5:
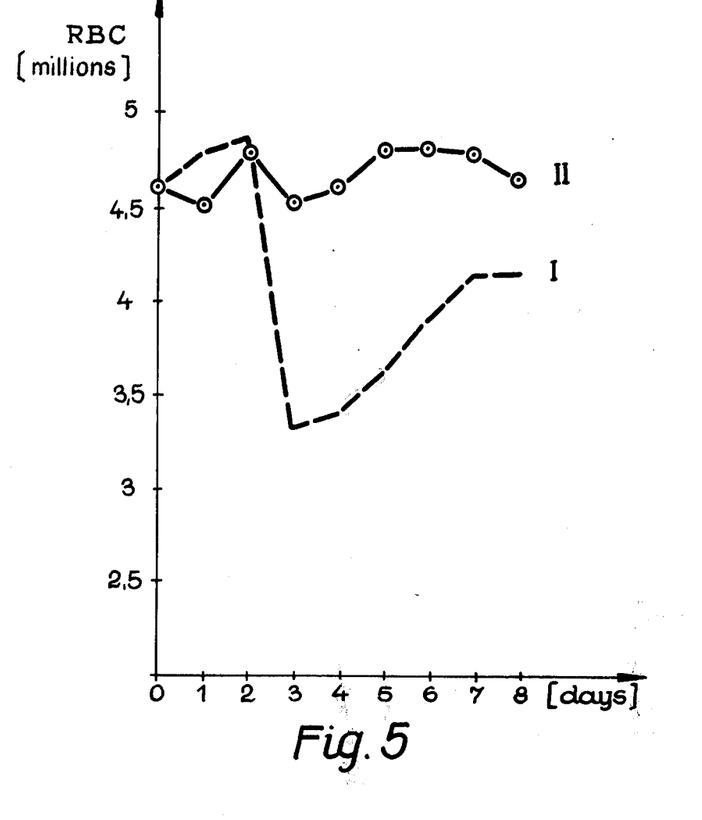

From Tables 1 to 3 and FIGS. 1 to 6 the following unexpected advantages of the compositions according to the invention in the treatment of animal subjects can be clearly seen:

(1) Although 2 to 3 days after the treatment a slight decrease in the number of the red blood cells can be observed, the extent of this decrease always remains below the decrease induced by the known cytostatics, when administered alone. Moreover, on the 3rd to 4th day following the treatment a regeneration can be observed and the number of the red blood cells approximates the control value (in the case of cyclophosphamide is equal to the control value already on the 4th day).

Figure 4:
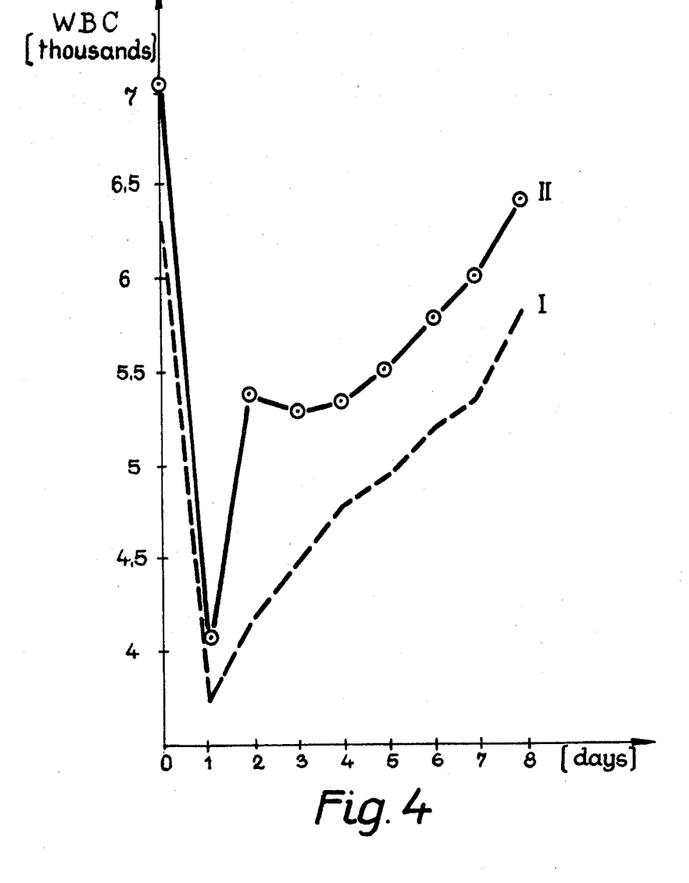

(2) The number of the white blood cells decreases on the second day subsequent to the treatment in the case of cyclophosphamide+TML and ritosulfanum+TML as well, but the restitution is relatively rapid and on the 8th day following the treatment the number of the white blood cells reaches the normal level.

Figure 6:
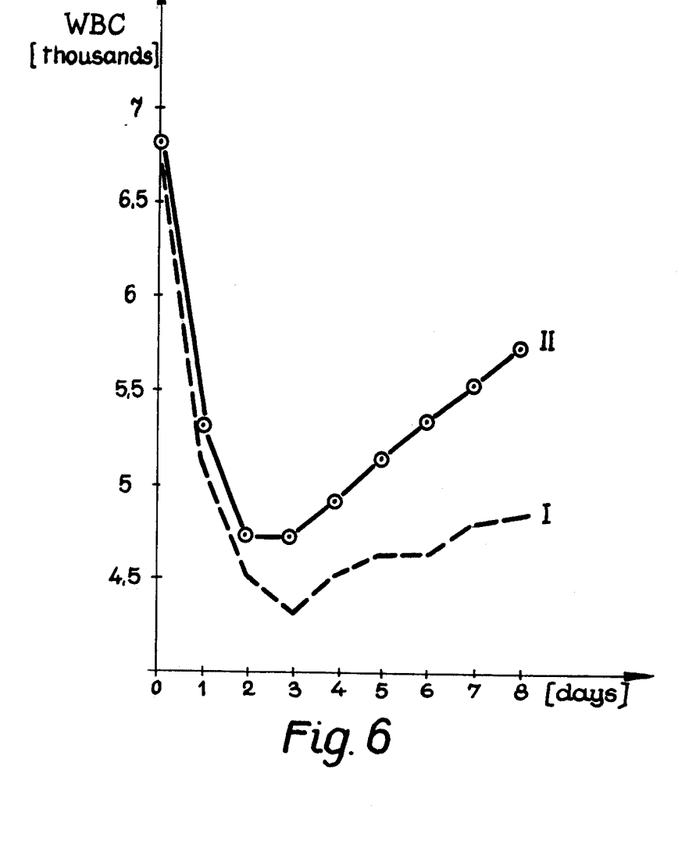

(3) When a combination of vincristine and TML is administered, the decrease in the number of red and white blood cells as well is considerably lower than in the animals which have been treated with vincristine alone.

The investigations on the blood count were carried out also with TMl-monoglutamate in the following manner:

(a) 12 healthy, 2 weeks old female CFLP mice (LATI) weighing 20 to 22 g. each were administered a single 30 mg./kg. of body weight i.p. dose of ritosulfanum. Half of the animals were treated also with a 100 mg./kg. of body weight i.p. dose of TML-monoglutamate. Following the treatment, on the 2nd, 4th, 7th, 10 th and 17th days the differential and quantitative blood counts were determined. Each of the measurements were performed on 3 mice, at 3 o'clock p.m., on an empty stomach. The results obtained are set forth in the Table 4. It is evident that the treatment with a combination according to the invention has an advantageous effect on the number of the red and white blood cells as well. The combinations practically have no influence on the lymphocyta:granulocyta proportion.

(b) 10 healthy, 8 weeks old of CFLP (LATI) female mice, weighing 20 to 22 g. each were administered a single 300 mg./kg. of body weight i.p. dose of cyclophosphamide. Half of the animals were treated also with a 100 mg./kg. of body weight i.p. dose of TML-monoglutamate, in addition to the administration of cyclophosphamide. The quantitative blood count was determined on the 4th and 10th days following the treatment. The results obtained are listed in Table 4. It can be seen that the number of the red blood cells in the group treated with the combination is higher than in the control group, which was given a cyclophosphamide treatment only.

TABLE 4

| Treatment | Day | Animals | RBC (millions/mm$^3$) | WBC (thousands/mm$^3$) |
|---|---|---|---|---|
| ritosulfanum alone | 2 | 1 | 7.0 | 3.600 |
| | | 2 | 6.8 | 3.200 |
| | | 3 | 7.2 | 3.400 |
| | | Average | 7.0 | 3.400 |
| | 4 | 1 | 5.6 | 3.400 |
| | | 2 | 6.8 | 6.200 |
| | | 3 | 6.4 | 5.200 |
| | | Average | 6.3 | 4.933 |
| | 7 | 1 | 4.6 | 5.600 |
| | | 2 | 4.0 | 2.600 |
| | | 3 | 6.4 | 4.000 |
| | | Average | 5.0 | 4.066 |
| | 10 | 1 | 7.4 | 11.800 |
| | | 2 | 2.8 | 10.600 |
| | | 3 | 5.6 | 6.600 |
| | | Average | 5.2 | 9.600 |
| | 17 | 1 | 6.7 | 5.200 |
| | | 2 | 6.0 | 5.000 |
| | | 3 | 6.2 | 5.100 |
| | | Average | 6.3 | 5.100 |
| ritosulfanum + TML-glutamate | 2 | 1 | 7.6 | 2.600 |
| | | 2 | 7.0 | 2.600 |
| | | 3 | 7.6 | 2.600 |
| | | Average | 7.4 | 2.600 |
| | 4 | 1 | 7.6 | 5.600 |
| | | 2 | 7.0 | 6.200 |
| | | 3 | 6.4 | 7.500 |
| | | Average | 7.0 | 6.366 |
| | 7 | 1 | 6.6 | 5.000 |
| | | 2 | 7.6 | 5.700 |
| | | 3 | 7.0 | 6.400 |

TABLE 4-continued

| Treatment | Day | Animals | RBC (millions/mm³) | WBC (thousands/mm³) |
|---|---|---|---|---|
| | | Average | 7.0 | 5.700 |
| | 10 | 1 | 5.8 | 11.800 |
| | | 2 | 5.6 | 8.000 |
| | | 3 | 5.2 | 9.000 |
| | | Average | 5.5 | 9.600 |
| | 17 | 1 | 10.0 | 10.400 |
| | | 2 | 9.6 | 10.800 |
| | | 3 | 9.2 | 10.600 |
| | | Average | 9.6 | 10.600 |
| cyclophosphamide alone | 4 | 1 | 5.4 | 8.600 |
| | | 2 | 6.0 | 3.500 |
| | | 3 | 7.2 | 7.200 |
| | | Average | 6.2 | 6.433 |
| | 10 | 1 | 4.8 | 18.000 |
| | | 2 | 4.4 | 16.000 |
| | | 3 | 9.2 | 14.000 |
| | | Average | 6.13 | 16.000 |
| cyclophosphamide + TML-glutamate | 4 | 1 | 7.8 | 6.600 |
| | | 2 | 8.2 | 4.400 |
| | | 3 | 7.0 | 9.000 |
| | | Average | 7.6 | 6.333 |
| | 10 | 1 | 6.8 | 16.000 |
| | | 2 | 9.6 | 16.000 |
| | | 3 | 5.6 | 19.100 |
| | | Average | 7.3 | 17.200 |

Since the toxic, in many instances lethal, effect of the cytostatic agents is substantially due to their damaging effect on the bone marrow, tests were carried out to determine the extent of the reduction of toxicity in the case of the compositions according to the invention compared with the toxicity of the various cytostatics and the $LD_{50}$-values. Three known cytostatic compounds, i.e. ritosulfanum, cyclophosphamide and vincristine were compared with the corresponding combinations containing also a TML-salt.

Tests were carried out on female DBA mice weighting 25 g. each. The test animals were divided into groups consisting of 5 mice, and each group was tested with a single i.p. dose of the compounds or compositions to be tested. The following doses were employed:

1. ritosulfanum 100 mg./kg.
2. ritosulfanum 67 mg./kg.
3. ritosulfanum 45 mg./kg.
4. ritosulfanum 30 mg./kg.
5. ritosulfanum 20 mg./kg.
6. ritosulfanum 100 mg./kg +TML 20 mg./kg.
7. ritosulfanum 67 mg./kg.+TML 20 mg./kg.
8. ritosulfanum 45 mg./kg.+TML 20 mg./kg.
9. ritosulfanum 30 mg./kg.+TML 20 mg./kg.
10. ritosulfanum 20 mg./kg.+TML 20 mg./kg.
11. cyclophosphamide 1012 mg./kg.
12. cyclophosphamide 675 mg./kg.
13. cyclophosphamide 450 mg./kg.
14. cyclophosphamide 300 mg./kg.
15. cyclophosphamide 200 mg./kg.
16. cyclophosphamide 1012 mg./kg. +TML 20 mg./kg.
17. cyclophosphamide 675 mg./kg.+TML 20 mg./kg.
18. cyclophosphamide 450 mg./kg.+TML 20 mg./kg.
19. cyclophosphamide 300 mg./kg.+TML 20 mg./kg.
20. cyclophosphamide 200 mg./kg.+TML 20 mg./kg.
21. vincristine 1 mg./kg.
22. vincristine 2 mg./kg.
23. vincristine 5 mg./kg.
24. vincristine 7 mg./kg.
25. vincristine 10 mg./kg.
26. vincristine 1 mg./kg.+TML 20 mg./kg.
27. vincristine 2 mg./kg.+TML 20 mg./kg.
28. vincristine 5 mg./kg.+TML 20 mg./kg.
29. vincristine 7 mg./kg.+TML 20 mg./kg.
30. vincristine 10 mg./kg.+TML 20 mg./kg.
31. ritosulfanum 50 mg./kg.+TML-glutamate 100 mg./kg.
32. vincristine 5 mg./kg.+TML-glutamate 100 mg./kg.
33. cyclophosphamide 600 mg./kg.+TML-glutamate 100 mg./kg.

In the first 10 days and on the 30st day following the treatment the number of the living animals was recorded. The results obtained are shown in the following Table 5.

TABLE 5

| Treatment | 1st | 2nd | 3rd | 4th | 5th | 6th | 7th | 8th | 9th | 10th | 30th |
|---|---|---|---|---|---|---|---|---|---|---|---|
| 1 | 1 | — | — | — | — | — | — | — | — | — | — |
| 2 | — | — | — | — | — | — | — | — | — | — | — |
| 3 | 5 | 5 | 5 | 5 | 4 | 4 | 3 | 2 | 2 | 2 | 2 |
| 4 | 5 | 5 | 5 | 5 | 5 | 5 | 5 | 5 | 5 | 5 | 5 |
| 5 | 5 | 5 | 5 | 5 | 5 | 5 | 5 | 5 | 5 | 5 | 5 |
| 6 | 1 | — | — | — | — | — | — | — | — | — | — |
| 7 | 1 | — | — | — | — | — | — | — | — | — | — |
| 8 | 5 | 5 | 5 | 4 | 2 | 2 | 1 | 1 | 1 | 1 | 1 |
| 9 | 5 | 5 | 5 | 5 | 5 | 5 | 5 | 5 | 5 | 5 | 5 |
| 10 | 5 | 5 | 5 | 5 | 5 | 5 | 5 | 5 | 5 | 5 | 5 |
| 11 | — | — | — | — | — | — | — | — | — | — | — |
| 12 | — | — | — | — | — | — | — | — | — | — | — |
| 13 | 4 | 3 | 3 | 3 | 2 | 2 | 1 | 1 | 1 | 1 | 1 |
| 14 | 5 | 5 | 5 | 5 | 5 | 5 | 5 | 5 | 5 | 5 | 5 |
| 15 | 5 | 5 | 5 | 5 | 5 | 5 | 5 | 5 | 5 | 5 | 5 |
| 16 | — | — | — | — | — | — | — | — | — | — | — |
| 17 | 1 | 1 | 1 | 1 | — | — | — | — | — | — | — |
| 18 | 4 | 4 | 4 | 3 | 3 | 3 | 2 | 1 | .1 | 1 | 1 |
| 19 | 5 | 5 | 5 | 5 | 5 | 5 | 5 | 5 | 5 | 5 | 5 |
| 20 | 5 | 5 | 5 | 5 | 5 | 5 | 5 | 5 | 5 | 5 | 5 |
| 21 | 5 | 5 | 5 | 5 | 5 | 5 | 5 | 5 | 5 | 5 | 5 |
| 22 | 5 | 5 | 5 | 5 | 5 | 5 | 5 | 5 | 5 | 5 | 5 |
| 23 | 5 | 5 | 4 | 4 | 4 | 4 | 4 | 3 | 3 | 3 | 3 |
| 24 | 5 | 5 | 5 | 5 | 5 | 5 | 5 | 5 | 5 | 5 | 5 |
| 25 | 5 | 5 | 5 | 5 | 2 | — | — | — | — | — | — |
| 26 | 5 | 5 | 5 | 5 | 5 | 5 | 5 | 5 | 5 | 5 | 5 |
| 27 | 5 | 5 | 5 | 5 | 5 | 5 | 5 | 5 | 5 | 5 | 5 |
| 28 | 5 | 5 | 5 | 5 | 5 | 5 | 5 | 4 | 4 | 4 | 4 |
| 29 | 5 | 5 | 5 | 5 | 5 | 5 | 5 | 5 | 5 | 5 | 5 |
| 30 | 5 | 5 | 5 | 5 | 5 | 5 | 5 | 4 | 4 | 4 | 4 |
| 31 | 5 | 5 | 5 | 5 | 5 | 5 | 5 | 5 | 5 | 5 | 4 |
| 32 | 5 | 5 | 5 | 5 | 5 | 5 | 4 | 4 | 3 | 3 | 3 |
| 33 | 5 | 5 | 5 | 5 | 5 | 5 | 5 | 5 | 5 | 5 | 3 |

From the above data it can be seen that substantially less animals died and the rate of death was also lower when the animals were treated with a combination of cyclophosphamide+TML and vincristine+TML, respectively than in case of the treatments carried out with cyclophosphamide and vincristine alone. The conclusion can be drawn that the pharmaceutical compositions according to the invention give a significant protection against the toxic side-effect exerted by cyclophosphamide or vincristine in animal subjects.

According to our experiments the combination of ritosulfanum and TML showed no lethality decreasing, protecting effect in comparison with ritosulfanum alone.

The effect of the instant compositions on the growth of the tumor cells was also tested. The tests were performed as follows:

155 CFLP female mice were injected (i.p.) with Ehrlich ascites tumor ($10^6$ tumour cells per animal). On the 10th day following the treatment the test animals were divided into groups and were given the following treatment:

(a) 30 mice were treated only with physiological sodium chloride solution (control);

(b) 25 mice were administered a single 20 mg./kg. i.p. dose of TML;

(c) 25 mice were administered a single 20 mg./kg. i.p. dose of cyclophosphamide;

(d) 25 mice were given a single 20 mg./kg. i.p. dose of ritosulfanum;

(e) 25 mice were administered a combination of 20 mg./kg. of cyclophosphamide and 20 mg./kg. of TML intraperitoneally, in a single dose;

(f) 25 mice were administered a combination of 20 mg./kg. of ritosulfanum and 20 mg./kg. of TML intraperitoneally, in a single dose.

In the above list the mg./kg. values indicate the mgs of the test compounds per kg. of body weight of the animals.

In four subsequent days following the treatment daily 3 animals were killed and the total number of the tumor cells present was determined.

The results obtained are set forth in the following Table 6.

TABLE 6

| Treatment | Number of the Ascites-Tumour cells on the | | | | |
|---|---|---|---|---|---|
| | 0th | 1st | 2nd | 3th | 4th |
| | day following the treatment | | | | |
| Control | $4.5 \times 10^8$ | $4.5 \times 10^8$ | $4.5 \times 10^8$ | $4.5 \times 10^8$ | $4.5 \times 10^8$ |
| TML | $4.5 \times 10^8$ | $6.2 \times 10^8$ | $8.0 \times 10^8$ | $5.5 \times 10^8$ | $5.0 \times 10^8$ |
| rito-sulfanum | $4.5 \times 10^8$ | $4.4 \times 10^8$ | $3.5 \times 10^8$ | $1.8 \times 10^8$ | |
| cyclo-phosph-amide | $4.5 \times 10^8$ | $4.5 \times 10^8$ | $3.6 \times 10^8$ | $4.0 \times 10^8$ | $5.8 \times 10^8$ |
| rito-sulfanum + +TML | | $4.4 \times 10^8$ | $6.0 \times 10^8$ | $0.2 \times 10^8$ | |
| cyclo-phosph-amide + TML | | $4.5 \times 10^8$ | $6.5 \times 10^8$ | $7.2 \times 10^8$ | $6.0 \times 10^8$ |

From the above data it can be seen that the total number of the tumor cells is substantially more reduced by a combination of TML and ritosulfanum than by ritosulfanum alone; while in the case of cyclophosphamide+TML-containing combinations a slight increase of the number of tumor cells can be observed, which is, however, negligible.

From the above experiments the conclusion can be drawn than the pharmaceutical compositions according to the invention decrease the undesired side-effects in animal subjects of the cytostatic compounds known in the art. It is especially important that the combinations eliminate or decrease the damage of the bone marrow and thus permit of increasing the dose of the cytostatic compound.

The actual daily dose of a known cytostatic agent in the compositions according to the invention is strongly dependent on the quality of the given cytostatic agent. For instance a daily dose for ritosulfanum is 20 to 40 mg./kg. of body weight, for cyclophosphamide amounts to 10 to 100 mg./kg. of body weight; for vincristine is 0.1 to 10 mg./kg. of body weight, preferably 1 to 5 mg./kg. of body weight. The TML is preferably employed in the form of its hydrochloride or monoglutamate salt. The most preferred compounds are L-N$^\epsilon$-trimethyllysin hydrochloride and monoglutamate, which are administered in a daily dose of 5 to 50 mg./kg., preferably of 20 to 40 mg./kg. of body weight, the exact dose depending on the route of administration on the condition of the patient to be treated, on the severity of the caes and on other similar factors. The pharmaceutical compositions according to the invention are preferably formulated in two different dosage forms; in the form of medium and strong unit doses, containing medium and high quantities of the cytostatic agents.

The proportions of the cytostatic agent to the N$^\epsilon$-trimethyllysin in the compositions according to the invention can vary between 1:1 and 1:100, depending on the usual dose of the given cytostatic agent. In the vincristine-, vinblastine- and N-formyl-leurosine containing compositions the proportion of the cytostatic agent to the N$^\epsilon$-trimethyllysin is between 1:10 and 1:100, while in the other compositions varies betwee 1:1 and 1:10.

The preferred compositions and the preparation of the pharmaceutical compositions according to the invention are illustrated by the following non-limiting Examples.

EXAMPLE 1

500 mg. of TML-glutamate, 500 mg. of N,N-bis(2-chloroethyl)-tetrahydro-2H-1,3,2-oxazophosphorine-2-amine-2-oxide (cyclophosphamide) and 200 mg. of protein-free gelatine are dissolved in distilled water of injection quality. The solution is adjusted to 35.0 ml and is then released from bacteria under aseptic conditions by filtration. From the sterile solution obtained 3.5-ml. portions are filled into 10-g. ampoule and the content of the ampoule is frozen at $-60°$ C. for 20 hours, lyophilized at $-45°$ C. in vacuo (25 mmHg) and is subsequently dried at $+20°$ C. for 10 hours.

The ampoules are then sealed with sterile rubber corks and are capsuled with aluminum caps. The compositions prepared in this way contain 50 mg. of TML-glutamate, 50 mg. of cyclophosphamide and 20 mg. of gelatine per dry-ampoules, sealed with rubber corks, in a lyophilized form. Prior to use for injection purposes the contents of an ampoule are dissolved in sterile distilled water or in an isotonic sodium chloride or glucose solution so that the total volume should be 10 ml.

EXAMPLE 2

500 mg. of TML-glutamate, 300 mg. of 1,4-di-(2-methylsulphonyloxyethylamino)-1,4-didesoxyerythrite dimethylsulphonate (ritosulfanum) and 400 mg. of gelatine are dissolved in distilled water of injection quality. The volume of the solution is adjusted to 10.0 ml. and it is further processed as described in Example 1, with the only different that 1-ml. portions are filled into the ampoules to be lyophilized. The composition obtained contains 50 mg. of TML-glutamate, 30 mg. of ritosulfanum and 40 mg. of gelatine per dry-ampoules sealed with rubber corks, in a lyophilized form.

EXAMPLE 3

500 mg. of TML-glutamate, 5 mg. of vincristine sulphate and 200 mg. of gelatine are dissolved in distilled water of injection quality and the final volume of the solution is adjusted to 10.0 ml. Then the procedure described in Example 2 is followed. The composition contains 50 mg. of TML-glutamate, 0.5 mg. of vincristine sulphate and 20 mg. of gelatine per dry ampoule sealed with 1 rubber cork, in a lyophilized form.

EXAMPLE 4

500 mg. of TML-glutamate, 5 mg. of vincristine sulphate, 80 mg. of polyvinylpyrrolidone and 365 mg. of mannite are dissolved in distilled water of injection quality and the final volume of the solution is adjusted to 10.0 ml. Then the procedure described in Example 2 is followed. The composition contains 50 mg. of TML-glutamate, 0.5 mg. of vincristine sulphate, 8 mg. of polyvinylpyrrolidone and 36.5 mg. of mannite per dry ampoule sealed with a rubber cork, in a lyophilized form.

EXAMPLE 5

50 mg. of TML-monoglutamate, 50 mg. of cyclophosphamide, 1 mg. of colloidal silicic acid, 1 mg. of magnesium stearate, 2 mg. of talc and 56 mg. of potato starch are admixed in the form of a dry powder until a homogenous mixture is obtained. The homogenous powder mixture weighing 160 mg. is then filled into hard gelatine capsules to afford a composition suitable for oral administration.

What we claim is:

1. A method of reducing toxic side effects in an animal subject treated with a compound selected from the group consisting of cyclophosphamide, ritosulfanum, vincristine, vinblastine, N-formylleurosine, and pharmaceutically effective salts thereof, which comprises administering to said subject in admixture with said compound, an amount of N$\epsilon$-trimethyllysine or a pharmaceutically acceptable salt thereof, in a ratio of 1:1 to 1:100 effective to reduce said toxic effects.

2. The method defined in claim 1 wherein said compound is vincristine, vinblastine or N-formylluerosine or a pharmaceutically effective salt thereof.

3. The method defined in claim 1 wherein the N$\epsilon$-trimethyllysine is used in the form of the monoglutamate salt thereof.

4. The method defined in claim 3 wherein the compound is vincristine.

* * * * *